US008017103B2

(12) United States Patent
Alderete et al.

(10) Patent No.: US 8,017,103 B2
(45) Date of Patent: Sep. 13, 2011

(54) **METHODS AND COMPOSITIONS TO DIAGNOSE *TRICHOMONAS* INFECTION**

(75) Inventors: John F. Alderete, San Antonio, TX (US); Te-Hung Chang, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 329 days.

(21) Appl. No.: 11/479,780

(22) Filed: Jun. 30, 2006

(65) Prior Publication Data

US 2007/0009974 A1    Jan. 11, 2007

Related U.S. Application Data

(60) Provisional application No. 60/695,903, filed on Jul. 1, 2005.

(51) Int. Cl.
*A61K 49/00* (2006.01)
*A61K 39/00* (2006.01)
*G01N 33/53* (2006.01)

(52) U.S. Cl. ............... 424/9.1; 424/269.1; 435/7.22

(58) Field of Classification Search ............. 435/7.22; 424/9.1, 269.1
See application file for complete search history.

(56) References Cited

U.S. PATENT DOCUMENTS

| | | | |
|---|---|---|---|
| 4,514,498 A | 4/1985 | Kettman et al. | |
| 4,707,442 A | 11/1987 | Alderete | |
| 4,861,711 A | 8/1989 | Friesen et al. | |
| 5,004,694 A | 4/1991 | Moay et al. | |
| 5,037,615 A | 8/1991 | Kane | |
| 5,330,897 A | 7/1994 | Pindak et al. | |
| 5,369,005 A | 11/1994 | Baseman et al. | |
| 5,415,994 A | 5/1995 | Imrich et al. | |
| 5,516,638 A | 5/1996 | Umovitz et al. | |
| 5,679,551 A | 10/1997 | Alderete | |
| 5,741,662 A | 4/1998 | Madsen et al. | |
| 5,776,694 A | 7/1998 | Sheiness et al. | |
| 5,876,985 A * | 3/1999 | Alderete | 435/6 |
| 5,879,881 A | 3/1999 | Rubenstein | |
| 5,922,563 A | 7/1999 | Alderete | |
| 6,063,905 A | 5/2000 | Capra et al. | |
| 6,174,293 B1 | 1/2001 | Buck et al. | |
| 6,207,395 B1 | 3/2001 | Valkirs et al. | |
| 6,528,321 B1 | 3/2003 | Fitzgerald et al. | |
| 6,824,975 B2 | 11/2004 | Hubscher et al. | |
| 2002/0045195 A1 | 4/2002 | Hubscher et al. | |
| 2003/0032029 A1 | 2/2003 | Collins | |
| 2003/0073147 A1 | 4/2003 | Alderete | |
| 2004/0072280 A1 | 4/2004 | Lawerence et al. | |
| 2006/0088892 A1 * | 4/2006 | Weart et al. | 435/7.22 |
| 2007/0009974 A1 | 1/2007 | Alderete et al. | |
| 2007/0015224 A1 | 1/2007 | Alderete et al. | |
| 2007/0077606 A1 | 4/2007 | Alderete et al. | |
| 2007/0134741 A1 | 6/2007 | Alderete et al. | |

FOREIGN PATENT DOCUMENTS

| | | |
|---|---|---|
| EP | 0 050 424 B1 | 4/1982 |
| EP | 0 810 436 A1 | 12/1997 |
| WO | WO 92/07096 A1 | 4/1992 |

OTHER PUBLICATIONS

Addis et al. (The Journal of Infectious Diseases, 1999; 180: 1727-30).*
Addis et al. "Host and Tissue Specificity of *Trichomonas vaginalis* Is Not Mediated by Its Known Adhesion Proteins" *Infection and Immunity* 68(7):4358-4360 (2000).
Addis et al. "Cloning and Molecular Characterization of a cDNA Clone Coding for *Trichomonas vaginalis* Alpha-Actinin and Intracelluar Localization of the Protein" *Infection and Immunity* 66(10):4924-4931 (1998).
Alderete and Garza "Soluble *Trichomonas vaginalis* Antigens in Cell-Free Culture Supernatants" *Molecular and Biochemical Parasitology* 13:147-158 (1984).
Alderete et al. "Cloning and Molecular Characterization of Two Genes Encoding Adhesion Proteins Involved in *Trichomonas vaginalis* Cytoadherence" *Molecular Microbiology* 17(1):69-83 (1995).
Alderete et al. "Monoclonal Antibody to a Major Surface Glycoprotein Immunogen Differentiates Isolates and Subpopulations of *Trichomonas vaginalis*" *Infection and Immunity* 52(1):70-75 (1986).
Alderete et al. "Phenotypes and Protein-Epitope Phenotypic Variation Among Fresh Isolates of *Trichomonas vaginalis*" *Infection and Immunity* 55(5):1037-1041 (1987).
Alderete et al. "Specific Parasitism of Purified Vaginal Epithelial Cells by *Trichomonas vaginalis*" *Infection and Immunity* 56(10):2558-2562 (1988).
Alderete "Identification of Immunogenic and Antibody-Binding Membrane Proteins of Pathogenic *Trichomonas vaginalis*" *Infection and Immunity* 40(1):284-291 (1983).
Alderete and Garza "Identification and Properties of *Trichomonas vaginalis* Proteins Involved in Cytadherence" *Infection and Immunity* 56(1):28-33 (1988).
Alderete and Kasmala "Monoclonal Antibody to a Major Glycoprotein Immunogen Mediates Differential Complement-Independent Lysis of *Trichomonas vaginalis*" *Infection and Immunity* 53(3):697-699 (1986).

(Continued)

*Primary Examiner* — Gary Nickol
*Assistant Examiner* — Lakia Tongue
(74) *Attorney, Agent, or Firm* — Myers Bigel Sibley & Sajovec, P.A.

(57) ABSTRACT

The present invention provides methods and compositions for diagnosing *Trichomonas* infection by detecting an antibody that specifically binds a *Trichomonas* α-actinin protein in a sample from a subject.

2 Claims, No Drawings

OTHER PUBLICATIONS

Alderete et al. "Heterogeneity of *Trichomonas vaginalis* and Discrimination among Trichomonal Isolates and Subpopulations with Sera of Patients and Experimentally Infected Mice" *Infection and Immunity* 49(3):463-468 (1985).

Alderete et al. "Phenotypic Variation and Diversity Among *Trichomonas vaginalis* Isolates and Correlation of Phenotype with Trichomonal Virulence Determinants" *Infection and Immunity* 53(2):285-293 (1986).

Alderete et al. "Only two of the *Trichomonas vaginalis* triplet AP51 adhesins are regulated by iron" *Microbial Pathogenesis* 24:1-16 (1998).

Alderete et al. "*Trichomonas vaginalis* Genetic Analysis of Cell Adherence" Abstract from CRISP website for Grant No. 2R21AI043940-05, Fiscal year 2003.

Alonzo and Pepe "Using a Combination of Reference Tests to Assess the Accuracy of a New Diagnostic Test" *Statistics in Medicine* 18:2987-3003 (1999).

Arroyo et al. "Molecular Basis of Host Epithelial Cell Recognition by *Trichomonas vaginalis*" *Molecular Microbiology* 6(7):853-862 (1992).

Arroyo et al. "Signalling of *Trichomonas vaginalis* for Amoeboid Tranformation and Adhesin Synthesis Follows Cytoadherence" *Molecular Microbiology* 7(2):299-309 (1993).

Arroyo et al. "Characterization of cDNAs Encoding Adhesin Proteins Involved in *Trichomonas vaginalis* Cytoadherence" *Archives of Medical Research* 26(4):361-369 (1995).

Baseman et al. "San Antonio STI TM CRC" Abstract from the CRISP website for Grant No. 2U19AI045429-06, Fiscal year 2004.

Benchimol et al. "Structure and Division of the Golgi Complex in *Trichomonas vaginalis* and *Tritrichomonas foetus*" *European Journal of Cell Biology* 80:593-607 (2001).

Bricheux et al. "Evidence for an uncommon α-actinin protein in *Trichomonas vaginalis*" *Molecular and Biochemical Parasitology* 95:241-249 (1998).

Checkoway et al. "Medical, Life-Style, and Occupational Risk Factors for Prostate Cancer" *The Prostate* 10:79-88 (1987).

Cogne et al. "Detection and Characterization of Serum Antitrichomonal Antibodies in Urogential Trichomoniasis" *Journal of Clinical Microbiology* 21(4): 588-592 (1985).

Cuatrecasas, Pedro "Protein Purification by Affinity Chromatography" *The Journal of Biological Chemistry* 245(12): 3059-3065 (1970).

Dalchau et al. "Monoclonal Antibody to a Human Leukocyte-Specific Membrane Glycoprotein Probably Homologous to the Leukocyte-Common (L-C) Antigen of the Rat" *Eur. J. Immunol.* 10:737-744 (1980).

Engbring et al. "Three genes encode distinct AP33 proteins involved in *Trichomonas vaginalis* cytoadherence" *Molecular Microbiology* 28(2):305-313 (1998).

Engbring et al. "Characterization of *Trichomonas vaginalis* AP33 adhesin and cell surface interactive domains" *Microbiology* 144:3011-3018 (1998).

Estrada et al. "Reporting and Concordance of Methodologic Criteria Between Abstracts and Articles in Diagnostic Test Studies" *JGIM* 15:183-187 (2000).

European Search Report for EP 03746064.9; dated Mar. 22, 2007.

Garber et al. "Immunogenic Proteins of *Trichomonas vaginalis* as Demonstrated by the Immunoblot Technique" *Infection and Immunity* 51(1):250-253 (1986).

Garber et al. "Cell Culture Compared with Broth for Detection of *Trichomonas vaginalis*" *Journal of Clinical Microbiology* 25(7):1275-1279 (1987).

Genzyme Diagnostics Product Information Sheet for OSOM *Trichomonas* Rapid Test. Printed from Genzyme website, Apr. 2007.

Hobbs et al. "Methods for Detection of *Trichomonas vaginalis* in the Male Partners of Infected Women: Implications for Control of Trichomoniasis" *Journal of Clinical Microbiology* 44(11):3994-3999 (2006).

Huppert et al. "Use of an immunochromatographic assay for rapid detection of *Trichomonas vaginalis* in vaginal samples" *J. Clin. Microbiol.* 43(2):684-687 (2005).

Huse et al. "Generation of a Large Combinatorial Library of the Immunoglobulin Repertoire in Phage Lambda" *Science* 246: 1275-1281 (1989).

International Search Report corresponding to International application No. PCT/US03/09474 filed Mar. 27, 2003.

Köhler and Milstein "Continuous Cultures of Fused Cells Secreting Antibody of Predefined Specificity" *Nature* 256:495-497 (1975).

Krieger et al. "Clinical Manifestations of Trichomoniasis in Men" *Annals of Internal Medicine* 118(11):844-849 (1993).

Kuberski et al. "Ankylosing Spondylitis Associated with *Trichomonas vaginalis* Infection" *Journal of Clinical Microbiology* 13(5):880-881.

Kuchnoor et al. "Adherence to Human Vaginal Epithelial Cells Signals for Increased Expression of *Trichomonas vaginalis* Genes" *Infection and Immunity* 73(10):6472-6478 (2005).

Lehker et al. "The Regulation by Iron of the Synthesis of Adhesins and Cytoadherence Levels in the Protozoan *Trichomonas vaginalis*" *J. Exp. Med.* 174:311-318 (1991).

Lehker and Sweeney "Trichomonad Invasion of the Mucous Layer Requires Adhesins, Mucinases, and Motility" *Sex Transm. Inf.* 75:231-238 (1999).

Lisi et al. "Monoclonal-Antibody-Based Enzyme-Linked Immunosorbent Assay for *Trichomonas vaginalis*" *Journal of Clinical Microbiology* 26(9):1684-1686 (1988).

Matthews et al. "Evaluation of Two Serological Tests for *Trichomonas vaginalis* Infection" *Journal of Clinical Microbiology* 17(5):840-843 (1983).

Miller et al. "Assessment of a rapid antigen detection system for *Trichomonas vaginalis* infection" *Clinical and Diagnostic Laboratory Immunology* 10(6):1157-8 (2003).

Mohamed et al. "Urine proves a poor specimen for culture of *Trichomonas vaginalis* in women" *Sex. Transm. Infect.* 77(1):78-79 (2001).

O'Brien et al. "Molecular Characterization of a Third Malic Enzyme-Like AP65 Adhesin Gene of *Trichomonas vaginalis*" *Microbial Pathogenesis* 20:335-349 (1996).

Patel et al. "Systematic Review of Diagnostic Tests for Vaginal Trichomoniasis" *Infectious Diseases in Obstetrics and Gynecology* 8:248-257 (2000).

Planned Parenthood Report "XenoStrip™-TV *Trichomonas* Test Clinical Efficacy Assessment" Xenotope Diagnostics, Inc. Jan. 25, 2004.

Ponce De Leon et al. "Relation Between Buccal Protozoa and pH and Salivary IgA in Patients with Dental Prothesis" *Rev. Inst. Med. Trop. S. Paulo* 43(4):241-242 (2001).

Rappelli et al. "Sequence of cDNA coding for a 65 kDa adhesive protein for the specific detection of *Trichomonas vaginalis* by PCR" *FEMS Microbiology Letters* 129:21-26 (1995).

Stary et al. "Detection of *Trichomonas vaginalis* on Modified Columbia Agar in the Routine Laboratory" *Journal of Clinical Microbiology* 40(9):3277-3280 (2002).

Sutcliffe et al. "Plasma antibodies against *Trichomonas vaginalis* and subsequent risk of prostate cancer" Abstract of poster presented at the 4th Annual American Association for Cancer Research International Conference entitled "Frontiers in Cancer Prevention Research." Baltimore, MD, Oct. 30-Nov. 2, 2005.

Van Der Schee et al. "Improved Diagnosis of *Trichomonas vaginalis* Infection by PCR Using Vaginal Swabs and Urine Specimens Compared to Diagnosis by Wet Mount Microscopy, Culture, and Flourescent Staining" *Journal of Clinical Microbiology* 37(12):4127-4130 (1999).

Wasserheit "Epidemiological Synergy: Interrelationships between Human Immunodeficiency Virus Infection and Other Sexually Transmitted Diseases" *Jn. Sex. Trans. Dis.* 19:61-77 (1992).

Watson-Jones et al. "High prevalence of trichomoniasis in rural men in Mwanza, Tanzania: results from a population based study" *Sex. Transm. Inf.* 76:355-362 (2000).

Watt et al. "Rapid Assay for Immunological Detection of *Trichomonas vaginalis*" *Journal of Clinical Microbiology* 24(4):551-555 (1986).

Wiese et al. "A meta-analysis of the Papanicolaou smear and wet mount for the diagnosis of vaginal trichomoniasis" *The American Journal of Medicine* 108(4):301-308 (1999).

Wos et al. "Immunoglobulin Isotypes of Anti-*Trichomonas vaginalis* Antibodies in Patients with Vaginal Trichomoniasis" *Journal of Clinical Microbiology* 24(5):790-795 (1986).

Yap et al. "Serum Antibodies to *Trichomonas vaginalis* in Invasive Cervical Cancer Patients" *Genitouria Med.* 71:402-404 (1995).

Zhang et al. "*Trichomonas vaginalis* and Cervical Cancer: A Prospective Study in China" *Ann. Epidemiol.* 5(4):325-332 (1995).

Dennis et al. "Meta-Analysis of Measures of Sexual Activity and Prostate Cancer" *Epidemiology* 13:72-79 (2002).

Rosenblatt et al. "Sexual Factors and the Risk of Prostate Cancer" *American Journal of Epidemiology* 153(12):1152-1158 (2001).

Sutcliffe et al. "Plasma Antibodies Against *Chlamydia trachomatis*, Human Papillomavirus, and Human Herpesvirus Type 8 in Relation to Prostate Cancer: a Prospective Study" *Cancer Epidemiol Biomarkers Prev.* 16(8):1573-1580 (2007).

Turkowicz et al. "Molecular Diagnosis of Oral Cavity Trichomonas Infections in HIV Patients" *Wiad Parazytol* 50(2):181-186 (2004) (Abstract only).

Miller. "Saliva Testing—A Nontraditional Diagnostic Tool" *Clinical Laboratory Science* 7(1):39-44 (1994).

\* cited by examiner

METHODS AND COMPOSITIONS TO DIAGNOSE *TRICHOMONAS* INFECTION

STATEMENT OF PRIORITY

This application claims the benefit, under 35 U.S.C. §119 (e), of U.S. Provisional Application No. 60/695,903, filed Jul. 1, 2005, the entire contents of which are incorporated by reference herein in their entirety.

BACKGROUND OF THE INVENTION

*Trichomonas vaginalis* causes vaginitis in women and non-gonococcal non-chlamydial urethritis in men. An estimated 5 million new cases of trichomonosis occur each year in the US, the majority in women. This sexually transmitted infection (STI) is associated with adverse outcomes in pregnancy. In addition, this STI may be associated with cervical cancer. Significantly, African Americans have the highest rates of trichomonosis than other American communities, and this STI contributes to the spread of HIV among women and minorities in the US. Epidemiologic studies suggest that *Trichomonas vaginalis* is associated with a 2- to 4-fold increased risk of HIV transmission, contributing to health disparities, and control of trichomonosis may be one of the most effective means of reducing HIV transmission risk worldwide.

Despite the impact of this STI to public health, fuindamental aspects of Trichomonas and parasite:cell biology and immunology remain unknown. An understanding of the urogenital antibody (Ab) response to *T. vaginalis* is incomplete in part because trichomonads secrete numerous cysteine proteinases into the vagina during infection, which degrade all Abs, leading to false or incomplete mucosal Ab results. The present invention overcomes previous shortcomings in the art by providing methods and compositions for detecting antibodies to *Trichomonas vaginalis* antigens in the saliva of both men and women as a diagnostic assay.

SUMMARY OF THE INVENTION

The present invention provides a method of diagnosing a *Trichomonas* infection in a subject, comprising: a) contacting saliva from the subject with a *Trichomonas* α-actinin protein under conditions whereby an antigen/antibody complex can form; and b) detecting formation of an antigen/antibody complex, thereby detecting an antibody that specifically binds a *Trichomonas* α-actinin protein in the sample and thereby diagnosing a Trichomonas infection in the subject.

Furthermore, the present invention provides a method of diagnosing a Trichomonas infection in a subject, comprising: a) contacting saliva from the subject with an antibody that specifically binds a *Trichomonas* α-actinin protein under conditions whereby an antigen/antibody complex can form; and b) detecting formation of an antigen/antibody complex, thereby detecting a *Trichomonas* α-actinin protein in the sample and thereby diagnosing a *Trichomonas* infection in the subject.

In addition, the present invention provides a method of detecting an antibody that specifically binds a *Trichomonas* α-actinin protein in a sample from a male subject, comprising: a) contacting the sample with a *Trichomonas* α-actinin protein under conditions whereby an antigen/antibody complex can form; and b) detecting formation of an antigen/antibody complex, thereby detecting the antibody.

Further provided is a method of diagnosing a *Trichomonas* infection in a male subject, comprising: a) contacting a sample from the subject with a *Trichomonas* α-actinin protein under conditions whereby an antigen/antibody complex can form; and b) detecting formation of an antigen/antibody complex, thereby detecting an antibody that specifically binds a *Trichomonas* α-actinin protein in the sample and thereby diagnosing *Trichomonas* infection in the subject.

In yet other embodiments, the present invention provides a method of diagnosing *Trichomonas* infection in a subject, comprising: a) contacting a sample from the subject with an antibody that specifically binds a *Trichomonas* α-actinin protein under conditions whereby an antigen/antibody complex can form; and b) detecting formation of an antigen/antibody complex, thereby diagnosing *Trichomonas* infection in the subject.

Further provided is a method of detecting a *Trichomonas* α-actinin protein in a sample, comprising: a) contacting the sample with an antibody that specifically binds a *Trichomonas* α-actinin protein under conditions whereby an antigen/antibody complex can form; and b) detecting formation of an antigen/antibody complex, thereby detecting the protein in the sample.

Additionally provided is a method of identifying an acute *Trichomonas* infection in a subject, comprising: a) at a first time point, contacting a first sample from the subject with a *Trichomonas* α-actinin protein under conditions whereby an antigen/antibody complex can form; b) detecting the formation of an antigen/antibody complex in step a); c) at a second time point, contacting a second sample from the subject with a *Trichomonas* α-actinin protein under conditions whereby an antigen/antibody complex can form; d) detecting the formation of an antigen/antibody complex in step (c); and e) comparing the amount of antibody of step (b) with the amount of antibody of step (d), whereby a difference in the amount of antibody identifies an acute *Trichomonas* infection in the subject.

DETAILED DESCRIPTION OF THE INVENTION

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The present invention is based on the unexpected discovery that infection with *Trichomonas vaginalis* can be diagnosed by detecting *Trichomonas vaginalis* α-actinin antigens and/or antibodies.

Thus, in some embodiments, the present invention provides a method of diagnosing a *Trichomonas* infection in a subject, comprising: a) contacting saliva from the subject with an antibody that specifically binds a *Trichomonas* α-actinin protein under conditions whereby an antigen/antibody complex can form; and b) detecting formation of an antigen/antibody complex, thereby detecting a *Trichomonas* α-actinin protein in the sample and thereby diagnosing a *Trichomonas* infection in the subject.

Also provided herein is a method of diagnosing a *Trichomonas* infection in a subject, comprising: a) contacting saliva from the subject with a *Trichomonas* α-actinin protein under conditions whereby an antigen/antibody complex can form; and b) detecting formation of an antigen/antibody complex, thereby detecting an antibody that specifically binds a *Trichomonas* α-actinin protein in the sample and thereby diagnosing a *Trichomonas* infection in the subject.

In other embodiments, the present invention provides a method of detecting an antibody that specifically binds a *Trichomonas* α-actinin protein in a sample from a male subject, comprising: a) contacting the sample with a *Trichomonas* α-actinin protein under conditions whereby an antigen/antibody complex can form; and b) detecting formation of an antigen/antibody complex, thereby detecting the antibody.

In additional embodiments, the present invention provides a method of diagnosing *Trichomonas* infection in a male subject, comprising: a) contacting a sample from the subject with a *Trichomonas* α-actinin protein under conditions whereby an antigen/antibody complex can form; and b) detecting formation of an antigen/antibody complex, thereby detecting an antibody that specifically binds a *Trichomonas* α-actinin protein in the sample and thereby diagnosing *Trichomonas* infection in the subject.

Additionally provided is a method of diagnosing *Trichomonas* infection in a subject, comprising: a) contacting a sample from the subject with an antibody that specifically binds a *Trichomonas* α-actinin protein under conditions whereby an antigen/antibody complex can form; and b) detecting formation of an antigen/antibody complex, thereby diagnosing *Trichomonas* infection in the subject.

Further provided is a method of detecting a *Trichomonas* α-actinin protein in a sample, comprising: a) contacting the sample with an antibody that specifically binds a *Trichomonas* α-actinin protein under conditions whereby an antigen/antibody complex can form; and b) detecting formation of an antigen/antibody complex, thereby detecting the *Trichomonas* α-actinin protein in the sample.

In some embodiments of this invention a method is provided, of identifying an acute *Trichomonas* infection in a subject, comprising: a) at a first time point, contacting a first sample from the subject with a *Trichomonas* α-actinin protein under conditions whereby an antigen/antibody complex can form; b) detecting the formation of an antigen/antibody complex in step a); c) at a second time point, contacting a second sample from the subject with a *Trichomonas* α-actinin protein under conditions whereby an antigen/antibody complex can form; d) detecting the formation of an antigen/antibody complex in step (c); and e) comparing the amount of antibody of step (b) with the amount of antibody of step (d), whereby a difference in the amount of antibody identifies an acute *Trichomonas* infection in the subject.

In this embodiment of identifying an acute infection in a subject, a first sample is taken at a first time point and a second sample is taken at a second time point and the amount of antibody and/or the type of antibody present in the two samples is compared. A change in the amount and/or type of antibody is indicative of an acute infection and no change in the amount and/or type of antibody is indicative of a past or chronic infection. For example, a decrease in the amount of antibody in the sample taken at the second time point (e.g., after treatment of the subject for a *T. vaginalis* infection) is indicative that the infection at the time the first sample was taken was an acute infection. Furthermore, if there is an increase in titer of antibody, this would indicate an ongoing/active infection that was not diagnosed initially or that was not eliminated upon diagnosis and drug treatment. This would necessitate additional examination of body sites and tissues for the presence of organism or antigen.

In the methods of this invention, the sample can be any biological fluid or tissue that can be used in an immunoassay of this invention, including but not limited to, serum, plasma, blood, saliva, semen, cerebrospinal fluid, semen, prostatic fluid, urine, sputum, joint fluid, body cavity fluid, whole cells, cell extracts, tissue, biopsy material, aspirates, exudates, vaginal washings, pap smear samples, pap smear preparations, slide preparations, fixed cells, tissue sections, etc.

In particular embodiments of this invention, the antibody employed in the methods of this invention is an antibody that specifically binds a *Trichomonas* α-actinin protein. A non-limiting example of an antibody that specifically binds a *Trichomonas* α-actinin protein is monoclonal antibody HA423 (Kucknoor et al. 2005. "Adherence to human vaginal epithelial cells signals for increased expression of *Trichomonas vaginalis* genes" *Infect Immun* 73:6472-6478 (2005)). Another non-limiting example of an antibody of this invention is monoclonal antibody ACT1. In certain embodiments, an antibody of this invention is not cross-reactive with human epithelial cell extracts or other protozoan protein extracts (e.g., *G. lambilia, E. histolytica, A. castellanii, L. major*). In further embodiments, an antibody of this invention has no, or minimal, crossreactivity with *T. tenax*. In yet other embodiments, an antibody of this invention does not bind or react with a *T. vaginalis* adhesin protein.

Furthermore, a *T. vaginalis* protein of this invention can be, but is not limited to a recombinant alpha actinin protein as described in the EXAMPLES section set forth herein, as well as peptides, fragments and immunologically similar variants of such proteins, peptides and fragments. Such proteins and peptides of this invention can be produced recombinantly according to methods well known in the art and can also be produced by fractionation and/or isolation techniques, synthesis techniques, etc. that are known for producing proteins and peptides for use in immunoassays.

The term "Trichomonas" as used herein, includes, but is not limited to a protozoan parasite of the order Trichomonadida, genera *Ditrichomonas, Trichomonas, Tritrichomonas* and *Pentatrichomonas*, comprising multiple species that infects both humans and animals. "*Trichomonas*" refers to any *Trichomonas* species, e.g., *Tritrichomonas foetus* (also known as *Trichomonas foetus, Tt. fetus*), *Tt enteris* and *T. paviovi*, which infect cattle; *Tt. suis, Tt. rotunda* and *T buttreyi*, which infect swine; *Dt. Ovis*, which infects sheep; *Tt. equi* and *T. equibuccalis*, which infect horses; *T. anatis, Tt. eberthi, T. gallinae* and *T. gallinarum*, which infect birds; *Tt. caviae, Tt muris, Tt. wenoni, Tt. Minuta* and *T. microti*, which infect rodents; *T. canistomae* and *T. felistomae*, which infect dogs and cats; and *T. tenax, T. vaginalis, Pt. hominis*, and *T. macacovaginae*, which infect primates (including humans). *Trichomonas vaginalis* as described herein includes isolate T016 (Type I) and isolate T068 (Type II), as well as any other *T. vaginalis* isolate now known or later identified.

The term "antibody" as used herein, includes, but is not limited to a polypeptide encoded by an immunoglobulin gene or immunoglobulin genes, or fragments thereof. "Antibody" also includes, but is not limited to, a polypeptide encoded by an immunoglobulin gene or immunoglobulin genes, or fragments thereof, which specifically binds to and recognizes the antigen-specific binding region (idiotype) of an antibody produced by the host in response to exposure to *Trichomonas* antigen(s).

The term "epitope" means an antigenic determinant that is specifically bound by an antibody. Epitopes usually consist of surface groupings of molecules such as amino acids and/or sugar side chains and usually have specific three-dimensional structural characteristics, as well as specific charge characteristics.

The terms "specifically binds to" and "specifically reactive with" refer to a binding reaction that is determinative of the presence of the antigen and antibody in the presence of a heterogeneous population of proteins and other biologics. Thus, under designated assay conditions, the specified antibodies and antigens bind to one another and do not bind in a significant amount to other components present in a sample. Specific binding to a target analyte under such conditions may require a binding moiety that is selected for its specificity for a particular target analyte. A variety of immunoassay formats may be used to select antibodies specifically reactive with a particular antigen. For example, solid-phase ELISA immunoassays are routinely used to select monoclonal antibodies specifically immunoreactive with an analyte. See Harlow and Lane (ANTIBODIES: A LABORATORY MANUAL, Cold Springs Harbor Publications, New York, (1988)) for a description of immunoassay formats and conditions that can be used to determine specific immunoreactivity. Typically a specific or selective reaction will be at least twice background signal to noise and more typically more than 10 to 100 times greater than background.

An "immunologically reactive fragment" of a protein refers to a portion of the protein or peptide that is immunologically reactive with a binding partner, e.g., an antibody, which is immunologically reactive with the protein itself.

Antibodies to *Trichomonas* proeins can be generated using methods that are well known in the art. Such antibodies can include, but are not limited to, polyclonal, monoclonal, chimeric, humanized, single chain, Fab fragments, and fragments produced by an expression library, including phage display. (See, e.g., Paul, FUNDAMENTAL IMMUNOLOGY, 3rd Ed., 1993, Raven Press, New York, for antibody structure and terminology.)

Antibody fragments that contain specific binding sites for a *Trichomonas* protein can also be generated. For example, such fragments include, but are not limited to, the F(ab')$_2$ fragments that can be produced by pepsin digestion of the antibody molecule, and the Fab fragments that can be generated by reducing the disulfide bridges of the F(ab')$_2$ fragments. Alternatively, Fab expression libraries can be constructed to allow rapid and easy identification of monoclonal Fab fragments with the desired specificity (Huse et al., *Science* 254, 1275-1281 (1989)).

For the production of antibodies, various hosts including goats, rabbits, rats, mice, humans, and others, may be immunized by injection with a *Trichomonas* proein (e.g., an α-actinin protein) or any fragment or oligopeptide or conjugate thereof that has immunogenic properties. Depending on the host species, various adjuvants can be used to increase the immunological response. Such adjuvants include, but are not limited to, Freund's complete and incomplete adjuvant, mineral gels such as aluminum hydroxide, and surface active substances such as lysolecithin, pluronic polyols, polyanions, peptides, oil emulsions, keyhole limpet hemocyanin, and dinitrophenol. Examples of adjuvants used in humans include BCG (bacilli Calmette-Guerin) and *Corynebacterium parvum*.

Monoclonal antibodies to *Trichomonas* proeins can be prepared using any technique that provides for the production of antibody molecules by continuous cell lines in culture. These include, but are not limited to, the hybridoma technique, the human B-cell hybridoma technique, and the EBV-hybridoma technique (Kohler et al. (1975) *Nature* 256:495-497; Kozbor et al. (1985) *J. Immunol. Methods* 81:31-42; Cote et al. (1983) *Proc. Natl. Acad. Sci.* 80:2026-2030; Cole et al. (1984) *Mol. Cell Biol.* 62:109-120). Briefly, the procedure is as follows: an animal is immunized with a *Trichomonas* proein or immunogenic fragment or oligopeptide or conjugate thereof. For example, haptenic oligopeptides of a Trichomonas protein can be conjugated to a carrier protein to be used as an immunogen. Lymphoid cells (e.g., splenic lymphocytes) are then obtained from the immunized animal and fuised with immortalizing cells (e.g., myeloma or heteromyeloma) to produce hybrid cells. The hybrid cells are screened to identify those that produce the desired antibody.

Human hybridomas that secrete human antibody can be produced by the Kohler and Milstein technique. Although human antibodies are especially preferred for treatment of humans, in general, the generation of stable human-human hybridomas for long-term production of human monoclonal antibody can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See Oi et al., *Bio Techniques* 4(4):214-221 (1986); Sun et al., *Hybridoma* 5 (1986).

The monoclonal antibodies of this invention specific for *Trichomonas* proein epitopes can also be used to produce anti-idiotypic (paratope-specific) antibodies. (See e.g., McNamara et al., *Science* 220, 1325-26 (1984); Kennedy et al., *Science* 232:220 (1986).) These antibodies resemble the *Trichomonas* proein epitope and thus can be used as an antigen to stimulate an immune response against the *Trichomonas* proein.

In addition, techniques developed for the production of "chimeric antibodies," the splicing of mouse antibody genes to human antibody genes to obtain a molecule with appropriate antigen specificity and biological activity can be used (Morrison et al. *Proc. Natl. Acad. Sci.* 81:6851-6855 (1984); Neuberger et al., *Nature* 312:604-608 (1984); Takeda et al., *Nature* 314:452-454 (1985)). Alternatively, techniques described for the production of single chain antibodies can be adapted, using methods known in the art, to produce Trichomonas protein-specific single chain antibodies. Antibodies with related specificity, but of distinct idiotypic composition, can be generated by chain shuffling from random combinatorial immunoglobin libraries (Burton, *Proc. Natl. Acad. Sci.* 88:11120-3 (1991)).

Antibodies can also be produced by inducing in vivo production in the lymphocyte population or by screening immunoglobulin libraries or panels of highly specific binding reagents as described in the literature (Orlandi et al., *Proc. Natl. Acad. Sci.* 86:3833-3837 (1989)); Winter et al., *Nature* 349:293-299 (1991)).

Various immunoassays can be used to identify antibodies of this invention having the desired specificity. Furthermore, a wide variety of immunoassays may be employed in the methods of this invention to detect antibodies and antigens of *Trichomonas* proeins for diagnosis of *Trichomonas* infection. Such immunoassays typically involve the measurement of antigen/antibody complex formation between a *Trichomonas* proein or peptide and its specific antibody.

The immunoassays of the invention can be either competitive or noncompetitive. In competitive binding assays, *Trichomonas* antigen or antibody competes with a detectably labeled *Trichomonas* antigen or antibody for specific binding to a capture site bound to a solid surface. The concentration of labeled antigen or antibody bound to the capture agent is inversely proportional to the amount of free antigen or antibody present in the sample.

Noncompetitive assays can be, for example, sandwich assays, in which the sample analyte (target antibody) is bound between two analyte-specific binding reagents. One of the binding agents is used as a capture agent and is bound to a solid surface. The other binding agent is labeled and is used to measure or detect the resultant antigen/antibody complex by e.g., visual or instrument means. A number of combinations of capture agent and labeled binding agent can be used. For instance, antigens derived from the *Trichomonas* can be used as the capture agent and labeled anti-human antibodies specific for the constant region of human antibodies can be used as the labeled binding agent to detect antibodies in a sample that bind the *Trichomonas* antigen. Goat, sheep and other non-human antibodies specific for human immunoglobulin constant regions are well known in the art. Alternatively, the anti-human antibodies can be the capture agent and the antigen can be labeled. Other proteins capable of specifically binding human immunoglobulin constant regions, such as protein A, protein L or protein G can also be used as the capture agent or labeled binding agent. These proteins are normal constituents of the cell walls of streptococcal bacteria. They exhibit a strong nonimmunogenic reactivity with immunoglobulin constant regions from a variety of species. (See, e.g., Kronval et al., *J. Immunol.*, 111:1401-1406 (1973); Akerstrom et al., *J. Immunol.*, 135:2589-2542 (1985).)

The non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or *Trichomonas* proeins can be conjugated or otherwise linked or connected (e.g., covalently or noncovalently) to a solid support (e.g., bead, plate, slide, dish, membrane or well) in accordance with known techniques. Antibodies can also be conjugated or otherwise linked or connected to detectable groups such as radio-labels (e.g., $^{35}S$, $^{125}I$, $^{32}P$, $^{3}H$, $^{14}C$, $^{131}I$), enzyme labels (e.g., horseradish peroxidase, alkaline phosphatase), gold beads, chemiluminescence labels, ligands (e.g., biotin) and/or fluorescence labels (e.g., fluorescein) in accordance with known techniques.

A variety of organic and inorganic polymers, both natural and synthetic can be used as the material for the solid surface. Nonlimiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, include paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, etc., immunoprecipitation, competitive binding assays and immunohistochemical staining. These and other assays are described, among other places, in Hampton et al. (Serological Methods, a Laboratory Manual, APS Press, St Paul, Minn. (1990)) and Maddox et al. (*J. Exp. Med.* 158:1211-1216 (1993)).

The methods of this invention can also be carried out using a variety of solid phase systems, such as described in U.S. Pat. No. 5,879,881, as well as in a dry strip lateral flow system, such as described, for example, in U.S. Patent Publication No. 20030073147, the entire contents of each of which are incorporated by reference herein.

A subject of this invention is any animal that can be infected by *Trichomonas vaginalis*. In certain embodiments, the subject is human.

In addition, a nucleic acid having the nucleotide sequence or a substantially similar nucleotide sequence of the gene encoding a *Trichomonas* proein of this invention can be used as a probe in a nucleic acid hybridization assay for the detection of a *Trichomonas* protein in various tissues or body fluids of a subject of this invention. The probe can be used in any type of nucleic acid hybridization assay including Southern blots (Southern, 1975, *J. Mol. Biol.* 98:508), Northern blots (Thomas et al., 1980, *Proc. Natl Acad. Sci.* U.S.A. 77:5201-05), colony blots (Grunstein et al., 1975, *Proc. Natl Acad. Sci.* U.S.A. 72:3961-65), slot blots, dot blots, etc. Stringency of hybridization can be varied depending on the requirements of the assay according to methods well known in the art. Assays for detecting nucleic acid encoding a *Trichomonas* proein in a cell, or the amount thereof, typically involve, first contacting the cells or extracts of the cells containing nucleic acids therefrom with an oligonucleotide probe that specifically binds to nucleic acid encoding a Trichomonas protein or peptide as described herein (typically under conditions that permit access of the oligonucleotide to intracellular material), and then detecting the presence or absence of binding of the oligonucleotide probe thereto. Any suitable assay format can be employed (see, e.g., U.S. Pat. No. 4,358,535; U.S. Pat. Nos. 4,302,204; 4,994,373; 4,486,539; 4,563,419; and 4,868, 104, the disclosures of each of which are incorporated herein by reference in their entireties).

The antibodies of this invention can be used in in vitro, in vivo and/or in in situ assays to detect a *Trichomonas* proein or peptide of this invention.

Also as used herein, the terms peptide and polypeptide are used to describe a chain of amino acids, which correspond to those encoded by a nucleic acid. A peptide usually describes a chain of amino acids of from two to about 30 amino acids and polypeptide usually describes a chain of amino acids having more than about 30 amino acids. The term polypeptide can refer to a linear chain of amino acids or it can refer to a chain of amino acids, which have been processed and folded into a functional protein. It is understood, however, that 30 is an arbitrary number with regard to distinguishing peptides and polypeptides and the terms may be used interchangeably for a chain of amino acids around 30. The peptides and polypeptides of the present invention are obtained by isolation and purification of the peptides and polypeptides from cells where they are produced naturally or by expression of a recombinant and/or synthetic nucleic acid encoding the peptide or polypeptide. The peptides and polypeptides of this invention can be obtained by chemical synthesis, by proteolytic cleavage of a polypeptide and/or by synthesis from nucleic acid encoding the peptide or polypeptide.

It is also understood that the peptides and polypeptides of this invention may also contain conservative substitutions where a naturally occurring amino acid is replaced by one having similar properties and which does not alter the function of the peptide or polypeptide. Such conservative substitutions are well known in the art. Thus, it is understood that, where desired, modifications and changes may be made in the nucleic acid and/or amino acid sequence of the peptides and polypeptides of the present invention and still obtain a peptide or polypeptide having like or otherwise desirable characteristics. Such changes may occur in natural isolates or may be synthetically introduced using site-specific mutagenesis, the procedures for which, such as mis-match polymerase chain reaction (PCR), are well known in the art. One of skill in the art will also understand that polypeptides and nucleic acids that contain modified amino acids and nucleotides, respectively (e.g., to increase the half-life and/or the therapeutic efficacy of the molecule), can be used in the methods of the invention.

"Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to a sequence that is naturally occurring or may include alternative codons that encode the same amino acid as that which is found in the naturally occurring sequence. Furthermore, nucleic acids may include codons that represent conservative substitutions of amino acids as are well known in the art. The nucleic acids of this invention can also comprise any nucleotide analogs and/or derivatives as are well known in the art.

As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide or polypeptide encoded by the nucleic acid are maintained.

The nucleic acid encoding the peptide or polypeptide of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid encoding a peptide and/or polypeptide of this invention.

The present invention further provides a vector comprising a nucleic acid encoding a peptide and/or polypeptide of this invention. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise, for example, viral nucleic acid including, but not limited to, vaccinia virus, adenovirus, retrovirus, alphavirus and/or adeno-associated virus nucleic acid. The nucleic acid or vector of this invention can also be in a liposome or a delivery vehicle, which can be taken up by a cell via receptor-mediated or other type of endocytosis.

The nucleic acid of this invention can be in a cell, which can be a cell expressing the nucleic acid whereby a peptide and/or polypeptide of this invention is produced in the cell. In addition, the vector of this invention can be in a cell, which can be a cell expressing the nucleic acid of the vector whereby a peptide and/or polypeptide of this invention is produced in the cell. It is also contemplated that the nucleic acids and/or vectors of this invention can be present in a host (e.g., a bacterial cell, a cell line, a transgenic animal, etc.) that can express the peptides and/or polypeptides of the present invention.

In some embodiments, for recombinant production of the chimeric polypeptides and/or peptides of this invention in prokaryotes, there are numerous *E. coli* (*Escherichia coli*) expression vectors known to one of ordinary skill in the art useful for the expression of nucleic acid encoding proteins or peptides of this invention. Other microbial hosts suitable for use include bacilli, such as *Bacillus subtilis*, and other enterobacteria, such as *Salmonella, Serratia*, as well as various *Psetidomonas species*. These prokaryotic hosts can support expression vectors that will typically contain sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence and have ribosome binding site sequences for example, for initiating and completing transcription and translation. If necessary, an amino terminal methionine can be provided by insertion of a Met codon 5' and in-frame with the coding sequence of the protein. Also, the carboxy-terminal extension of the protein can be removed using standard oligonucleotide mutagenesis procedures.

Additionally, yeast expression systems and baculovirus systems, which are well known in the art, can be used to produce the chimeric peptides and polypeptides of this invention.

The vectors of this invention can be transferred into a cell by well-known methods, which vary depending on the type of cell host. For example, calcium chloride transfection is commonly utilized for prokaryotic cells, whereas calcium phosphate treatment, lipofection or electroporation can be used for other cell hosts.

The present invention further provides a kit for detection of alpha actinin antibodies and/or proteins of this invention. Such a kit can comprise one or more antibodies of this invention, along with suitable buffers, wash solutions, dilution buffers, secondary antibodies, detection reagents, etc. for the detection of antigen/antibody complex formation under various conditions. In another embodiment, a kit of this invention can comprise a polypeptide, a peptide, an antigenic fragment and/or a fusion protein or peptide comprising an alpha actinin epitope, along with suitable buffers, wash solutions, dilution buffers, secondary antibodies, detection reagents, etc. for the detection of antigen/antibody complex formation under various conditions.

The present invention is more particularly described in the Examples set forth below, which are not intended to be limiting of the embodiments of this invention.

EXAMPLES

Example 1

Detection of *Trichomonas vaginalis* Proteins and Antibodies in Saliva

Patient saliva has Ab specific to whole cell *T. vaginalis* and P230. An ELISA was carried out, in which microtiter wells were coated with either whole *T. vaginalis* cells or with *T. vaginalis* P230 protein purified with the mAb DM126. Saliva of individual *T. vaginalis*-infected patients and pooled saliva of healthy, uninfected individuals were then tested for reactive IgG using HRP-conjugated anti-human IgG secondary Ab. Each patient had elevated absorbance values compared to the control pooled saliva of uninfected individuals. This study demonstrates the presence of IgG Ab reactive to whole trichomonads and to the P230 protein. Wells coated with whole cells and P230 were tested separately using rabbit anti-*T. vaginalis* serum or with mAb DM126 for standardization and to show similar reactions among wells.

Minimal crossreactivity of saliva Ab between *T. vaginalis* and *T. tenax*. It is expected that the existence of immunocrossreactive antibodies in saliva of patients to *T. tenax*, the oral trichomonad will be minimal or non-existent. *T. tenax* organisms are not readily apparent in the oral cavity and are not detectable in most individuals even if there is severe periodontitis.

In this experiment, pooled, highly-reactive saliva of three individual patients, 34, 45 and 114, that gave equally high absorbance values with the whole cell-ELISA were used. In wells coated with whole *T. tenax*, the same-pooled saliva reacted minimally. The extent of reactivity with an absorbance of 0.025 was similar to that seen for control saliva from uninfected individuals.

Saliva IgG and IgA react similarly with the two naturally occurring types of isolates of *T. vaginalis*. A Western blot analysis was conducted to identify the specific *T. vaginalis* proteins detected by the saliva Ab of patients and to examine whether the proteins detected by the saliva Ab were similar for the two naturally occurring types of isolates, as defined by infection with the dsRNA viruses (57, 74). This was significant because, despite the commonality of protein profiles among the isolates types, the dsRNA virus infection significantly influences the protein-antigen profiles of trichomonads (57). What is desired, therefore, is identification of trichomonad antigens that are common among isolates and to which all patients make Ab.

Total proteins of *T. vaginalis* isolate T016 (Type 1) *T. vaginalis* T068 (Type 2) were blotted onto nitrocellulose after SDS PAGE. Triplicate blots were prepared using identical protein preparations prior to probing two blots with pooled saliva from patients and one blot with pooled saliva from uninfected individuals. One duplicate blot probed with patient saliva was then incubated with the IgG fraction of anti-human IgG antibodies and the second blot was probed with anti-human IgA antibodies. The control blot was incubated with the IgG fractions of both anti-human IgG and IgA. The saliva was diluted 1:20 in PBS containing detergent extract equal to $10^7$ *T. tenax* organisms.

Numerous *T. vaginalis* proteins were detected by saliva Ab regardless of the isolate type and by both IgG and IgA. Several bands recognized by Ab had common electrophoretic mobilities for both the virus-positive (Type II) and virus-minus (Type I) trichomonads. Both IgG and IgA antibodies to trichomonad antigens were found in saliva of patients.

Demonstration of specific anti-*T. vaginalis* Ab in saliva of patients. Standard enzyme-linked immunosorbent assays (ELISA) will demonstrate the existence of saliva Ab in all patients. The assays will be optimized to take into account any crossreactive Ab to *T. tenax* and to monitor the level of saliva Ab among the patients. Three different assays will provide a basis by which to determine the level of Ab to trichomonad proteins in saliva. ELISA protocols that bind non-specific sites on the coated wells with irrelevant proteins such as BSA and/or or skim milk will be employed. The first ELISA has whole intact trichomonads coated onto 96-well microtiter plates as antigen for saliva Ab detection, and this whole cell-ELISA will employ standard conditions. The second ELISA will have purified IgG of high-titered rabbit antisera to total trichomonad proteins coated onto microtiter wells. Then, trichomonad protein antigens bound to the IgG-coated wells after incubation with detergent extracts of *T. vaginalis* will provide antigen detectable by saliva Ab. Similarly, the third assay will have a cocktail of mAbs coated onto microtiter wells. These mAb-coated wells will bind antigen from the trichomonal extract, and these parasite proteins bound to mAbs will serve as antigen for saliva Ab. The second and third sandwich-ELISAs assume that saliva Ab will be directed to epitopes different from those of rabbit antiserum and mAbs. After treatment of freshly prepared ELISA plates with skim milk to decrease non-specific interactions, select samples of saliva from patients and from uninfected control individuals will be diluted in PBS containing *T. tenax* extract prior to addition of standard 100 μl volumes to microtiter wells. PBS without *T. tenax* extract will provide duplicates of the same saliva. Initial data on the extent of crossreactivity between saliva Ab and *T. tenax* will be obtained, although preliminary data suggests the concern regarding crossreactivity is minimal. Initial experiments indicate that 2 hr incubation at 37° C. is optimal. After washing, horseradish peroxidase-conjugated secondary anti-IgG, anti-IgA, or Ig (IgG+IgA+IgM) Ab will be added, followed by color development with substrate.

Purified trichomonad protein P230 that is the prominent immunogen in the vaginal Ab response will serve as a positive control for saliva Ab.

Saliva Ab from women with trichomonosis during infection and after treatment will be tested. Saliva will be obtained on at least two occasions post-treatment to assess the nature of Ab response following removal of trichomonads from the urogenital tract. Saliva from male partners of infected women will also be examined.

Some of the antigens recognized by saliva Abs may be glycoproteins. Thus, it may be necessary to treat the antigen with periodate to remove carbohydrate moieties. Periodate-treated whole trichomonads will also be used as a source of antigen to confirm the reactivity of saliva Abs to protein. Likewise, a water-soluble extract of *T. vaginalis* will be treated with periodate prior to dialysis and this antigen without carbohydrate will be added to the Ab-coated wells.

Analysis of existing hybridoma libraries for mAbs that detect protein-antigens reactive by saliva Ab. Two sandwich-ELISAs will be used to analyze a hybridoma cell library of >50 different mabs for reaction with trichomonad proteins also detected by saliva Ab. Either Protein A or the IgG fraction of anti-human Ig (anti-IgG, anti-IgA and anti-IgM) prepared in sodium carbonate will be coated onto wells of microtiter plates overnight using standard procedures. Then, removal of Ab to *T. tenax* proteins from pooled saliva will be done by incubating saliva beforehand with preparative blots of *T. tenax* proteins. The preabsorbed saliva Ab will then be added to the coated wells. After treatment with a detergent extract of *T. vaginalis* proteins and extensive washing, the individual wells will be incubated with hybridoma supernatant containing mAb and processed accordingly. Microtiter wells can be coated with equal amounts of the IgG fraction of goat anti-human Igs. Through optimization of the assay using several available mAbs, including DM126 to P230 as a control, three sets of mAbs defined on the basis of level of reactivity from high (mAb hybridoma 1), medium (mAb hybridoma 4) and low (mAb hybridoma 10) have been identified, and these will also serve as controls.

One goal of this invention is a saliva Ab diagnostic test that detects active infection. Thus, mAbs to trichomonad proteins highly reactive with saliva Ab during infection, but not following treatment, are preferred. Therefore, once mAbs reactive with parasite proteins bound by the saliva Ab in this sandwich-ELISA are found, retesting will be carried out following the availability of recombinant protein to coat wells or by coating wells with the mAbs for a sandwich-ELISA. Saliva Ab from patients during infection and post-treatment will be examined identically to identify a particular protein antigen that meets these criteria. This will be important for obtaining the cDNA to produce a recombinant antigen and for preparing a diagnostic assay.

New hybridomas producing mAbs will also be prepared according to art-known methods. The procedure to immunize mice will be based on knowledge of the trichomonad proteins detected by saliva Ab in immunoblot or immunoprecipitation assays. As above, once the mAb or mAbs are identified that are similarly reactive to trichomonad proteins as the Ab in saliva of male and female partners with trichomonosis, the mAbs can be used as described herein in a sandwich-ELISA.

Determining the identity of the specific $T.$ *vaginalis* proteins reactive with saliva Ab and comparison of saliva Ab reactivity with the two naturally occurring isolate types. Standard immunoblot (IB) and radioimmunoprecipitation (RIP) assays for $T.$ *vaginalis* can be used to identify the trichomonad proteins recognized by saliva Ab. Pooled saliva from patients will be used to probe nitrocellulose blots with total trichloroacetic acid-precipitated parasite proteins. The REP assay can accommodate more readily individual saliva samples, and the RIP assay will use a detergent extract of either intrinsically- or extrinsically-labeled organisms. As with the ELISAs described above, both IB and RIP assays will also use saliva from uninfected individuals and patients with other STIs for comparison. Experiments with $T.$ *tenax*-preabsorbed saliva will be performed early to determine the necessity for adding $T.$ *tenax* extract to the saliva prior to either IB or RIP. As noted above, trichomonads or extracts will be treated with periodate as necessary to remove carbohydrate prior to IB and RIP. These IB and RIP assays will affirm that saliva Ab reacts to trichomonad proteins.

Monoclonal antibodies that bind trichomonad proteins have been extensively characterized. On the basis of the electrophoretic mobility of the protein antigens, mAbs can be selected that react with proteins of the same size as saliva Ab. Then, Protein A-Sepharose or magnetic beads coated with Protein A treated with mAbs can be used to deplete extracts of particular proteins prior to IB and RIP with saliva Ab. A decreased intensity or elimination of a band after protein depletion followed by IB and/or RIP with patient saliva will suggest strongly that saliva Ab was toward this protein removed by the mAb. Likewise, appearance of a band will show that saliva Ab was to a different trichomonad protein.

Obtaining samples. In preliminary experiments it was determined that saliva can be obtained through various methods without affecting the quality of reactivity of Ab that is present. Saliva can be obtained using a large absorbent swab placed in the mouth for several minutes. This will result in accumulation of several milliliters of saliva. The large swab can then be placed in a tube with 2 ml to 3 ml of PBS and stored at 4° C. After accumulating numerous swab saliva samples, the tubes and sera from individuals can be transported immediately to the laboratory for processing. If necessary, both saliva and serum can be stored at −70° C. before using in the various assays. An alternative to the large swab for accumulation of saliva is the collection of several milliliters of spit directly into a sterile conical test tube. The saliva samples can be centrifuged to remove any debris prior to examination in the various assays.

Generation of subtractive cDNA library of $T.$ *vaginalis*. This subtraction strategy differentiates the uniquely expressed genes of $T.$ *vaginalis* from those of $T.$ *tenax*. For this purpose, cDNA from $T.$ *vaginalis* will be subtracted to cDNA from $T.$ *tenax*. The cDNA of specific transcripts of $T.$ *vaginalis* is the "tester" population and the reference cDNA of $T.$ *tenax* is the "driver" population. Reverse transcribed MRNA samples will produce a pool of cDNAs from $T.$ *vaginalis* and $T.$ *tenax*. Restriction endonuclease digestion of the double-stranded cDNA will give short cDNA fragments and prevent preferential PCR amplification of naturally occurring small cDNAs. Both ends of each cDNA fragment will then be ligated with specific linkers. In the following PCR amplification steps, both tester and driver cDNAs will be made for each sample to allow subtraction in both directions. Tester cDNA will be radiolabeled to monitor the efficiency of subtractions. The driver cDNA that is biotinylated using bio-11-UTP will permit for the separation of hybrids and driver by streptavidin. Tester cDNA will be mixed with a 100-fold excess of driver cDNA, denatured and allowed to reanneal during the hybridization step. After annealing, tester/driver (cDNA/mRNA) and driver-unhybridized polyA-RNA are removed by adding streptavidin and phenol extraction. Unhybridized tester or tester hybrids will be retained in the aqueous phase, which is enriched for differentially expressed genes. A first hybridization between an excess of driver and limited amount of tester will lead to equalization and enrichment of differentially expressed sequences in the tester population. During the second hybridization, the aqueous phase from the primary hybridization will be used as templates for PCR amplification of a new set of testers and drivers, which is the next round of hybridization. Subtractions performed will occur over a short period of time (2 h) to remove sequences that are common and abundant in both $T.$ *vaginalis* and $T.$ *tenax* or a much longer time (40 h) to remove rare sequences that are common to both trichomonal species. A series of alternating short and long hybridizations will be performed and progress of subtractions will be monitored by the amount of radioactive tracer that has been retained in the aqueous phase after the phenol extractions. Subtractions will be stopped when radioactive tracer is no longer removed in the aqueous phase. The subtracted cDNA fraction can then be cloned into a λZap Express™ vector (Stratagene) using the restriction sites incorporated in the adaptors and packaged with a Gigapack Gold λ packaging extract to create a $T.$ *vaginalis* specific cDNA library.

In order to estimate the efficiency of the subtracted cDNA population, the abundance of known genes, before and after subtraction, will be compared. For this purpose, the house keeping gene glyceraldehyde-3-phosphate dehydrogenase (GAPDH) (EC.1.2.2.12), which is common to both $T.$ *vaginalis* and $T.$ *tenax*, will be amplified. As a positive control for subtraction, a conserved 650-bp repeat region that is unique to $T.$ *vaginalis* will be used. Quantitative RT-PCR analyses for the known genes, GAPDH and 650-bp repeats will confirm differential expression. In addition, it will be confirmed that the subtracted cDNA library is a true reflection of what exists in vivo, by Northern blot analysis of total RNA from *T. vaginalis* and *T. tenax*. The probes will be GAPDH and 650-bp repeat sequences.

Screening the subtractive cDNA library. The availability of the subtractive cDNA library will permit screening for cDNAs encoding *T. vaginalis* proteins reactive with saliva Abs. Pre-absorbing the saliva Ab by mixing with a detergent extract, incubating with fixed T tenax parasites, or adsorbing saliva with preparative blots of *T. tenax* proteins will reduce background signals due to *T. tenax*. Preabsorbed saliva Ab will be assessed for absorption efficiency, by means of dot-blots using *T. tenax* whole cells or lysate. The subtractive cDNA library will be screened with preabsorbed Ab. Briefly, the λ-phage library will be mixed with XL-1 blue bacterial cells and plated on agar plates. The filters will be lifted in duplicates and used for screening. Positive clones will be further analyzed for protein expression. Positive clones will be selected and subjected to in vivo excision to isolate the plasmid from the λ-phage clones. Plasmid DNA will be isolated following excision and sequenced. The genome sequence data of *T. vaginalis* will be used to identify the open reading frames and thereby obtain the recombinant protein.

Evaluation of isolated clones for specificity using *T. vaginalis* specific mAbs. mAbs will be used for further screening to confirm the specificity of the positive clones obtained by screening with saliva Abs. This will be performed in parallel with the saliva Ab as outlined in the previous experiment. The duplicate filters will be incubated with the selected mAbs. The positive signals obtained will be super-imposed with that of the original signals obtained from the saliva Ab. By doing so, the specificity of clones will be checked, which can recognize both the saliva Ab and the mAb. Northern analyses can also be carried out, using the clones as probes to detect positive mRNA expression in *T. vaginalis* and negative expression in *T. tenax*. In addition, quantitative RT-PCR analyses can be done, using specific primers derived from the positive clones. Alternatively and as an additional control, mAbs immunocrossreactive with *T. tenax* can be used in immunoblot experiments with both trichomonal species.

Two-dimensional (2-D) protein analysis for isolating unique *T. vaginalis* protein immunogens. Unique *T. vaginalis* proteins can also be isolated by using one of the modern proteomic tools of 2-D gel electrophoresis, coupled with mass spectroscopy. Furthermore, pooled saliva can be used to screen 2-D immunoblots of both *T. vaginalis* and *T. tenax*. In combination with 2-D gel electrophoresis, matrix-associated laser desorption/ionization-time of flight mass spectrometry (MALDI-TOF-MS) is particularly suitable for the identification of protein spots via mass fingerprint or microsequencing. This method allows a detailed analysis of post-translational protein modifications, thereby enabling studies on functional aspects of different proteins. Mass spectroscopy of the spots unique to *T. vaginalis* will provide sufficient amino acid sequence data to analyze the particular open reading frame from the available genome sequence. Total protein extracts of $^{35}$S-labeled proteins of both *T. vaginalis* and *T. tenax* will be subjected to 2-D electrophoresis and processed accordingly. Spot reading software will dissect unique spots to be excised from the gel and digested, and peptides will be sequenced for protein identification.

Characterization of select *T. vaginalis*-unique cDNAs. Full-length cDNAs will be obtained using 5'- and 3'-RACE. The sequences of full-length clones will be compared to the GenBank databases using BLASTN, BLASTX and BLASTP. If possible, the cDNAs will be named according to homologous sequences in the database. Metabolic pathways will be identified using the website of KEGG Metabolic Pathways. Unknown sequences will further be analyzed for putative protein domains and/or signal sequences using the Expasy site. The cDNAs will be compared with the *Trichomonas* genome sequence where information can be obtained on the ORF, related genes and copy number.

In order to confirm the ORF of unknown genes, in vitro translation will be performed using a TNT-coupled reticulocyte lysate in vitro translation system, which will verify the size of putative protein products. Clones will be selected for the generation of recombinant proteins and the partial and/or full-length coding sequences of the selected cDNA clones will be ligated into pET26B plasmid vector (Novagen) and transformed in bacterial host BL21 (DE3). This vector carries signal sequences that facilitate the export of recombinant protein into the periplasmic space, which promotes proper folding and disulfide bond formation that in turn enhances the solubility and activity of target proteins. In addition, the pET26B vector has a 6-His tag at the C-terminal end of the recombinant protein.

The functions of the newly identified genes and the role that the protein may play in terms of host protection and mucosal Ab response will be analyzed.

Recombinant protein detection by saliva Ab. Preparative purification of the trichomonad antigen can be done using a tagged fusion recombinant protein. It may not be necessary for the recombinant protein to be full size, especially if the subclone protein is detected by saliva Ab. Comparisons can be made between the recombinant protein and the natural protein for qualitative and quantitative differences in saliva Ab reactivity. The purified recombinant or trichomonad protein can be plated onto microtiter wells or dot-blotted onto nitrocellulose for detection by saliva Ab. Optimization comparing the intensity of signals between saliva Ab and the mAb can be performed side by side, and the assay can be standardized by knowing the minimum amount of antigen giving an unambiguous positive signal.

Although this approach is straightforward, the use of one or several distinct trichomonad proteins for saliva Ab diagnosis will be based on the extent and nature of Ab responses to the individual proteins. As such, this will require a careful analysis of the amount of Ab to each antigen in the saliva of patients. Further, the selection of antigen will be based on the significant decrease in amount of Ab after one week post-treatment. Earlier report showed that vaginal Ab detected the protein immunogen P230 during infection and after treatment. Therefore, this protein can serve as a control. It is not certain what amount of decrease in Ab concentration will be necessary, and this will have to be experimentally determined through the analysis of patient saliva. It will be important that control, uninfected individuals or patients with other STIs do not have crossreactive Ab to the protein(s) being evaluated.

Diagnostic test to show proof of principle for candidate protein detecting saliva Ab. It is an embodiment of this invention to employ the antigens and antibodies of this invention to produce a lateral flow diagnostic test wherein components react and migrate to a series of zones and banding patterns, thereby providing information relevant to the diagnosis. With the saliva Ab test, a flow through device can be employed, in which trichomonad antigens of this invention are impregnated onto a small-defined surface within a larger surface that will permit simple, sequential addition of diluted saliva followed by detectably-conjugated mAb(s). This can be done, for example, by using standard protocols as described by the manufacturer of such test device components and membrane components (Schleicher and Schuell Co., Keene, N.H.). At a distinct site on the membrane, the P230 protein can also be included as an internal control. The same membrane can also have a negative irrelevant antigen for specificity. This prototype can be used to provide proof of principle for a saliva diagnostic test for *Trichomonas vaginalis* infection.

Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference into this application in order to more fully describe the state of the art to which this invention pertains.

What is claimed is:

1. A method of detecting an antibody that specifically binds a *Trichomonas* α-actinin protein in a sample from a male subject, comprising:

a) contacting the sample from the male subject with a *Trichomonas* α-actinin protein under conditions whereby an antigen/antibody complex can form; wherein the sample is saliva; and b) detecting formation of an antigen/antibody complex, thereby detecting the antibody.

2. A method of detecting an antibody that specifically binds a *Trichomonas* α-actinin protein in saliva from a subject, comprising:

a) contacting saliva from the subject with a *Trichomonas* α-actinin protein under conditions whereby an antigen/antibody complex can form; and b) detecting formation of an antigen/antibody complex, thereby detecting the antibody.

* * * * *

UNITED STATES PATENT AND TRADEMARK OFFICE
CERTIFICATE OF CORRECTION

| | | |
|---|---|---|
| PATENT NO. | : 8,017,103 B2 | Page 1 of 1 |
| APPLICATION NO. | : 11/479780 | |
| DATED | : September 13, 2011 | |
| INVENTOR(S) | : Alderete et al. | |

It is certified that error appears in the above-identified patent and that said Letters Patent is hereby corrected as shown below:

Column 8, Line 44: Please correct "proein or" to read -- protein or --

Column 12, Line 25: Please indent as a new paragraph starting with "After treatment"

Column 13, Line 38: Please correct "The REP assay" to read -- The RIP assay --

Column 15, Line 61: Please correct "Characterization ofselect"
to read -- Characterization of select --

Signed and Sealed this
Thirty-first Day of January, 2012

David J. Kappos
*Director of the United States Patent and Trademark Office*